(12) United States Patent  (10) Patent No.: US 6,573,721 B1
Cull  (45) Date of Patent: Jun. 3, 2003

(54) TIME DOMAIN ELECTROMAGNETIC ANALYSIS AND INSPECTION SYSTEM FOR CONDUITS

(75) Inventor: James Phillip Cull, Vermont South (AU)

(73) Assignee: Rock Solid Research Pty. Ltd., Burwood (AU)

( * ) Notice: Subject to any disclaimer, the term of this patent is extended or adjusted under 35 U.S.C. 154(b) by 0 days.

(21) Appl. No.: 09/869,876

(22) PCT Filed: Jan. 13, 2000

(86) PCT No.: PCT/AU00/00017

§ 371 (c)(1),
(2), (4) Date: Jul. 6, 2001

(87) PCT Pub. No.: WO00/42425

PCT Pub. Date: Jul. 20, 2000

(30) Foreign Application Priority Data

Jan. 13, 1999 (AU) .................................. PP8134

(51) Int. Cl.⁷ .............................. G01V 3/08; G01V 3/10
(52) U.S. Cl. ..................... 324/336; 324/239; 324/238
(58) Field of Search ............................... 324/326, 238, 324/239, 240, 241, 242, 243, 220, 232, 219, 362, 226, 262, 329, 336; 702/56

(56) References Cited

U.S. PATENT DOCUMENTS

| | | | |
|---|---|---|---|
| 4,855,677 A | * | 8/1989 | Clark, Jr. et al. ............ 324/238 |
| 5,119,023 A | | 6/1992 | Lloyd |
| 5,302,895 A | | 4/1994 | Philpot |
| 5,796,253 A | * | 8/1998 | Bosnar et al. ............... 324/238 |
| 6,239,593 B1 | * | 5/2001 | Burkhardt et al. .......... 324/233 |

FOREIGN PATENT DOCUMENTS

| | | |
|---|---|---|
| EP | 0301906 | 2/1989 |
| EP | 580485 | 1/1994 |
| GB | 2269673 | 2/1994 |
| WO | 96/34279 | 10/1996 |

* cited by examiner

*Primary Examiner*—Edward Lefkowitz
*Assistant Examiner*—Subhash Zaveri
(74) *Attorney, Agent, or Firm*—Volpe and Koenig, P.C.

(57) ABSTRACT

An inspection system include a transmitter and a receiver configured for communication with a remotely positioned processing means. The transmitter and receiver are arranged as a mobile apparatus configured for insertion into any duct, conduit, pipeline, mining shaft, or the like, or any diameter or cross section. The transmitter is configured to transmit an electromagnetic signal to induce an electromagnetic response in the duct and the electromagnetic response is detected by the receiver. The mobile apparatus is self-powered and processes the electromagnetic response prior to communicating the processed response to the remotely positioned processing means as a discrete signal.

17 Claims, 6 Drawing Sheets

| CH | T(ms) | SAMPLES |
|---|---|---|
| 1 | .05 | 5 |
| 2 | .10 | 5 |
| 3 | .15 | 5 |
| 4 | .20 | 5 |
| 5 | .275 | 10 |
| 6 | .375 | 10 |
| 7 | .475 | 10 |
| 8 | .575 | 10 |
| 9 | .725 | 20 |
| 10 | .925 | 20 |
| 11 | 1.125 | 20 |
| 12 | 1.325 | 20 |
| 13 | 1.625 | 40 |
| 14 | 2.025 | 40 |
| 15 | 2.425 | 40 |
| 16 | 2.825 | 40 |
| 17 | 3.425 | 80 |
| 18 | 4.225 | 80 |
| 19 | 5.025 | 80 |
| 20 | 5.825 | 80 |
| 21 | 7.025 | 160 |
| 22 | 8.625 | 160 |
| 23 | 10.225 | 160 |
| 24 | 11.825 | 160 |
| 25 | 14.225 | 320 |

TIME DOMAIN ELECTROMAGNETIC ANALYSIS AND INSPECTION SYSTEM FOR CONDUITS

FIELD OF THE INVENTION

The present invention relates broadly to a subsurface inspection probe and, in particular, to a subsurface pipeline inspection system for inspecting pipe bedding surrounding subsurface pipelines.

BACKGROUND

Traditionally, subsurface pipelines such as sewerlines and storm water drains have been inspected using manual access. This involves a person entering the pipeline system and carrying out a manual inspection of pipe walls. However, this method reveals only surface defects in the pipe walls and gives no information on defects in the surrounding soils. This method also has inherent dangers and health risks for the person carrying out the inspection.

Remote Controlled Closed Circuit Television (CCTV) has also been employed in inspecting subsurface pipelines. This method involves the use of a small camera which is mounted on the end of along flexible cable. The camera is placed into the pipeline through an access opening and is then remotely controlled from the surface. This method removes the dangers involved in a person entering the pipeline, however, this method again reveals only surface defects in the pipe walls and gives no information on defects in the surrounding soils.

In order to inspect the bedding of a subsurface pipeline and to detect defects in the surrounding soils, more elaborate techniques have been employed such as ground probing radar (GPR) and seismic methods. The GPR systems consist of a transmitting antenna emitting electromagnetic radiation (Ie: generated by an oscillator), a receiving antenna and an energy detecting device, or receiver. A portion of the transmitted signal is intercepted by a reflecting object, such as the wall of the pipeline, and is reradiated in all directions. The energy reradiated in the back direction is collected by the receiving antenna and delivered to a receiver, where it is processed to detect the presence of the pipeline. The time taken for the radar signal to travel through the pipeline and back is measured. Defects in the soil surrounding the pipeline, which can result in deformation or collapse of the pipeline, are detected by using the time measurement and known soil characteristics, and comparing this information to site drawings.

Seismic methods, including techniques such as tomography, measure the velocity and refraction of seismic waves in a manner similar to the electromagnetic radiation measurements of GPR. However, seismic methods are based on long wavelengths with a resulting reduction in resolution. Further, both the GPR and seismic methods require complex equipment and processing which results in low productivity and unacceptably high costs.

SUMMARY OF THE INVENTION

It is an object of the present invention to substantially overcome, or at least ameliorate, one or more of the deficiencies of the above mentioned arrangements.

According to one aspect of the present invention there is provided, a time domain electromagnetic (TEM) subsurface analysis system characterized by at least part of said system being configured for insertion along a sub-surface conduit for emission and reception of TEM signals.

According to another aspect of the present invention there is provided a time domain electromagnetic (TEM) subsurface analysis system characterized by a mobile TEM signal transmitter and receiver module operatively coupled to a stationary controller and TEM recorder module and by said mobile module being self-powered and processing said electromagnetic response prior to communicating the processed response to said stationary controller.

According to still another aspect of the present invention there is provided a time domain electromagnetic (TEM) subsurface analysis system incorporating at least one transmitter coil and a plurality of receiver coils characterized in that said coils are configured as part of a mobile module including a multiplexer arrangement for coupling at least said receiver coils in a predetermined manner to a recorder module.

According to still another aspect of the present invention there is provided an inspection system comprising a transmitter and a receiver configured for communication with a remotely positioned processing means, said transmitter and receiver being arranged as a mobile apparatus configured for insertion into a duct, and said transmitter being configured to transmit an electromagnetic signal to induce an electromagnetic response in said duct, said electromagnetic response being detected by said receiver, characterized in that, said mobile apparatus is self-powered and processes said electromagnetic response prior to communicating the processed response to said remotely positioned processing means as a discrete signal.

According to still another aspect of the present invention there is provided an inspection system, said system comprising:
  a first apparatus configured for insertion into a duct and comprising:
    (i) transmission means for transmitting an electromagnetic signal to induce an electromagnetic response in said duct and material surrounding said duct;
    (ii) detection means for detecting said electromagnetic response;
    (iii) conversion means for converting said electromagnetic response to a discrete signal; and
    (iv) communication means for reading and communicating said discrete signal to a second apparatus positioned remotely to said first apparatus;
  said second apparatus comprising:
    (i) storage means for storing said discrete signal;
    (ii) processor for processing said discrete signal; and
    (iii) display for displaying said processed discrete signal.

According to still another aspect of the present invention there is provided a method of inspecting a subsurface pipeline utilizing an inspection system, said system comprising:
  a first apparatus configured for insertion into a duct and comprising:
    (i) transmission means for transmitting an electromagnetic signal to induce an electromagnetic response in said duct and material surrounding said duct;
    (ii) detection means for detecting said electromagnetic response;
    (iii) conversion means for converting said electromagnetic response to a discrete signal; and
    (iv) communication means for reading and communicating said discrete signal to a second apparatus positioned remotely to said first apparatus;
  said second apparatus comprising:

(i) storage means for storing said discrete signal;
(ii) processor for processing said discrete signal; and
(iii) display for displaying said processed discrete signal, said method comprising the steps of transmitting a first electromagnetic signal from said transmission means;
detecting a second electromagnetic signal at said detection means;
amplifying said second electromagnetic signal;
sampling said amplified signal;
converting said sampled signal to a digital signal utilizing said conversion means;
communicating said digital signal from said first apparatus to said second apparatus;
storing said digital signal in said storage means; and
displaying said digital signal on said display.

BRIEF DESCRIPTION OF THE DRAWINGS

An embodiment of the present invention will now be described with reference to the accompanying drawings in which.

Figure 1:
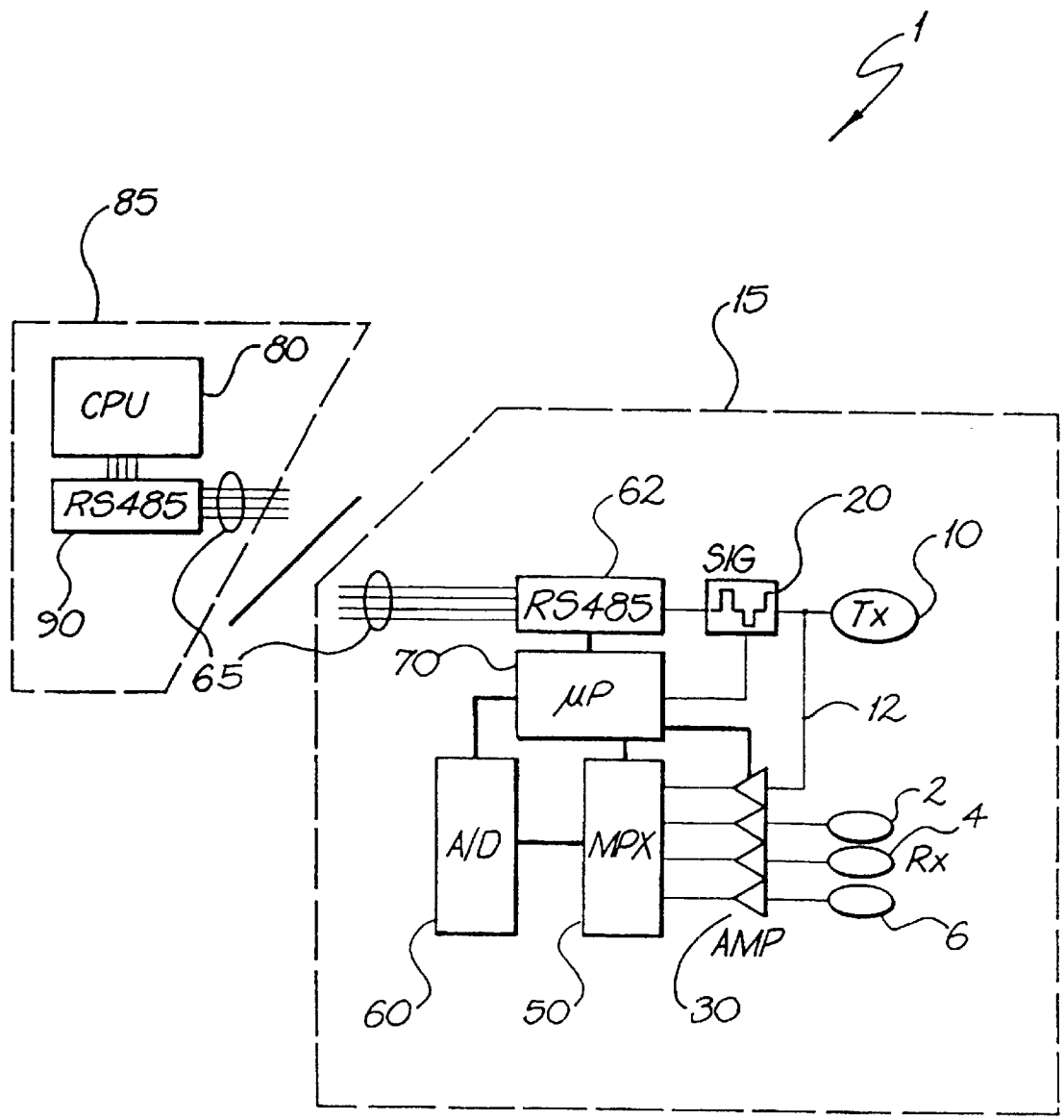
FIG. 1 is a schematic block diagram representation of the subsurface pipeline inspection system of the preferred embodiment.

Appendix 1 is a pseudo-code listing of A/D control according to the system of FIG. 1.

DETAILED DESCRIPTION OF THE DRAWINGS

The preferred embodiment is a time domain electromagnetic (TEM) subsurface pipeline inspection system for inspecting the bedding of subsurface -sewerlines. An electromagnetic wave transmitter and receiver are arranged within a self-contained module which is linked to a stationary control center using a communications cable. The transmitter disseminates a square wave electromagnetic field and the receiver detects a resulting secondary field generated by subsurface conductors. The inspection system thus directly measures soil deformation by extracting information that is contained in the secondary field.

FIG. 1 shows an overall block diagram of the pipeline inspection system 1 of a first embodiment. The pipeline inspection system 1 includes a mobile unit 15, insertable into the pipeline, and a stationary unit 85, generally configured near the entrance to the pipeline and connectable to the mobile unit 15 via a communications cable 65. The mobile unit 15 includes a transmitter 10 connected to a signal generator 20 which provides bipolar switching for transmitter currents of up to 10 amps. The signal applied to the transmitter 10 is also connected, via line 12, to a first parallel stage of a variable gain amplifier/filter 30. Connected to second, third and fourth parallel stages of the variable gain amplifier/filter 30 is a receiver 40 having corresponding receiver elements 2, 4, 6 configured to detect TEM signals. The elements 2, 4, 6 are formed by inductor coils wound on preset mutually perpendicular formers (see FIGS. 6(a) and (b)), to allow for 3-dimensional scanning. Each coil has 900 turns on a cross section of 100 mm diameter. The elements 2, 4, 6 are connected to a second, third and fourth stage of the variable gain amplifier/filter 30, respectively. Each output of the first, second, third or fourth stages of the variable gain amplifier/filter 30 is fed into a multiplexer 50. The multiplexer 50 is configured to select alternative ones of the stage outputs for sampling by an A/D converter 60. The A/D converter 60 provides a minimum of 12 bits resolution at a sampling rate of 100 kHz combined with gain ranging to ensure an equivalent 21 bits (signed) for each input after linear stacking of multiple transmitter cycles. A microprocessor 70 provides control for the A/D converter 60, transmitter 10, multiplexer 50 and signal generator 20. The microprocessor 70 also provides gain control as well as communicating, via an RS485 transceiver 62 and cable 65, with the stationary unit 85 which includes a remotely positioned stationary computer 80 positioned outside a pipeline and an RS485 transceiver 90. The amplifier/filter 30 is configured for signal conditioning in order to record actual transmitter 10 current. In series with each output of the variable gain amplifier/filter 30 is a reference tap to a standard 1 ohm resistor (not shown), in series with the transmitter loop, giving a voltage proportional to the transmitter current. The microprocessor 70 addresses each multiplexer 50 channel in turn to monitor the 3D signal normalized for the transmitter current. The stationary computer 80 provides control and data storage for the system 1.

Figure 2:
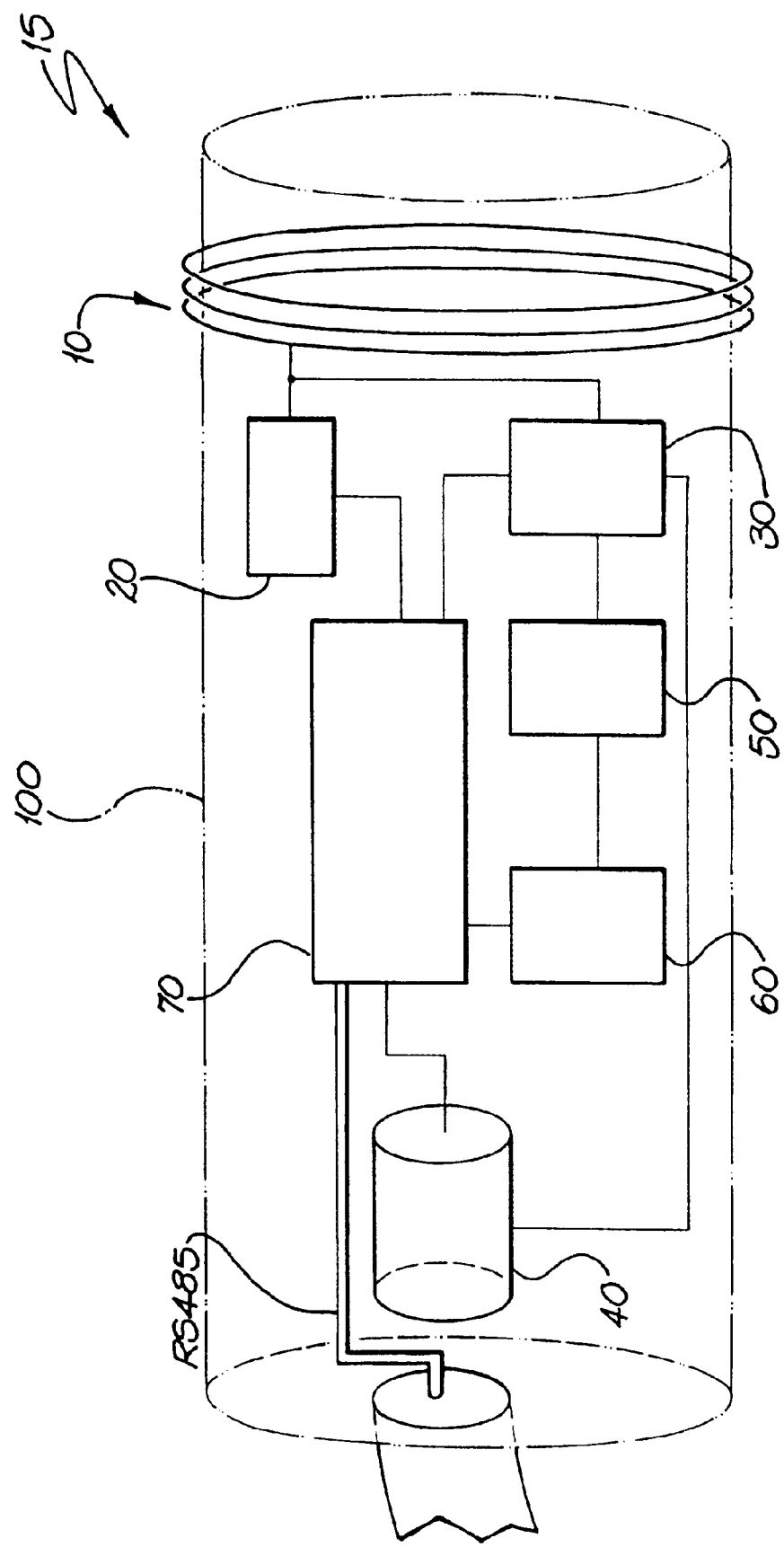
FIG. 2 is a drawing showing a radial transmitter and a detector mounted on a housing according to the system of FIG. 1.

FIG. 2 shows the physical configuration of the mobile unit 15 where the transmitter 10 is formed as a radial winding of 50 turns around one end of a cylindrical plastic housing 100. The receiver 40 is mounted at the opposing end of the housing 100. The housing 100 also contains the signal generator 20, variable gain amplifier/filter 30, multiplexer 50, A/D converter 60 and microprocessor 70. The communications cable 65 is connected to one end of the housing 100. The housing 100 is preferably constructed of PVC or similar material which is selected for resistance to abrasion as well as being fully sealed for immersion in liquid. In the preferred embodiment, the diameter of the housing is preferably 150 mm and the transmitter and receiver are spaced apart by a distance of 500 mm. The dimensions of the housing 100 and the separation of the transmitter 10 and receiver 40 may vary according to the dimensions of the subsurface passage. In an alternative configuration, the transmitter 10 and receiver 40 may be mounted in separate housings linked by a flexible cable (not illustrated) to allow for flexibility in negotiating any corners in the sewerline pipe. Power is supplied to the signal generator by two 12 volt batteries 32, 34 (See FIGS. 6(a) and (b)) contained in the housing 100.

Figure 6A:
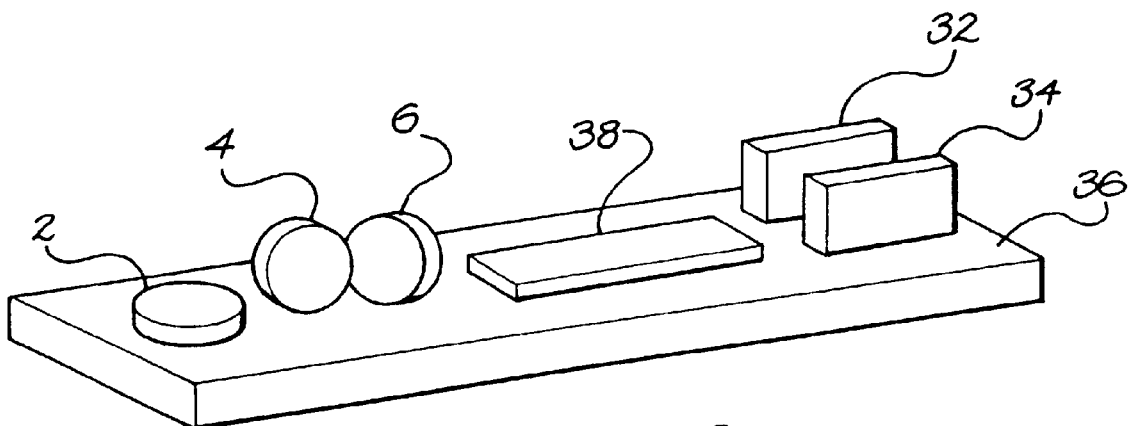
FIGS. 6(a) and 6(b) show a perspective and a plan view of internal components, of the system of FIG. 1, mounted on a support.
Figure 6B:
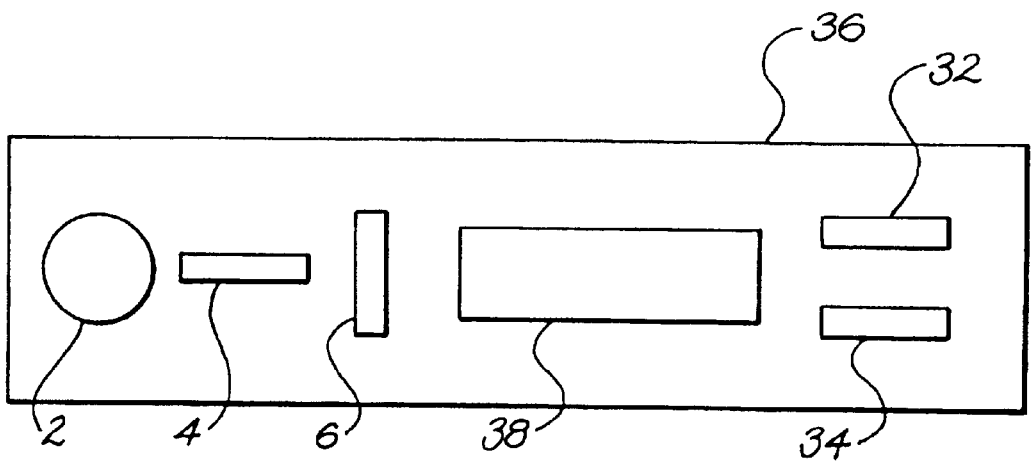

As seen in FIG. 6(a), the internal components of the housing 100 are mounted on a support 36. The mutually perpendicular elements 2,4,6 are mounted at one end of the support 36 with the batteries 32, 34 mounted at the other end. As stated earlier, the configuration of the elements 2, 4, 6 allows for three dimensional scanning. A control circuit 38 which includes the signal generator 20, variable gain amplifier/filter 30, multiplier 50, A/D convertor 60 and microprocessor 70, is positioned between the batteries 32, 34 and the elements 2,4,6. FIG. 6(b) is a plan view of the support 36 with the elements 2, 4, 6, the batteries 32, 34 and the control circuit 38 mounted thereon.

The preferred embodiment is configured for incremental progression through a sewerline. The housing 100 with the radial transmitter 10 and receiver 40 are manually lowered into a sewerline through an access hole in the line. The housing 100 is then manually advanced through the sewerline utilizing tow ropes (not shown) or –a cable (not shown), which can be connected directly to the housing 100 through which the communications cable 65 is run. Data readings are taken at 2 m intervals with the housing 100 kept stationary during each reading to assist with noise reduction. Random rotations of the cylindrical housing 100 can occur causing cross-pipe components to become confused. In one embodiment, a rotation sensing device such as an arrangement of accelerometer devices (not illustrated) can be mounted to the housing 100 to allow for suitable corrections.

Figure 3:
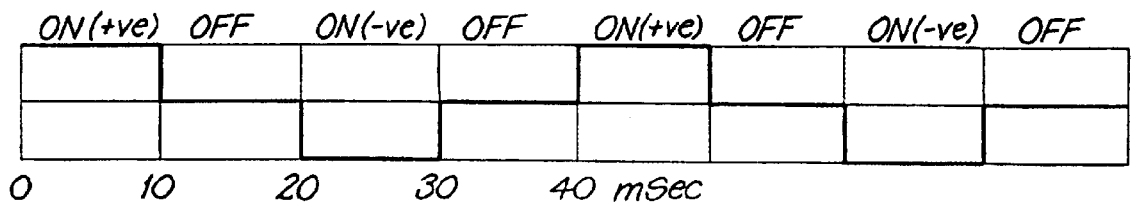
FIG. 3 represents an on-off transmitting current based on a square wave pulse according to the system of FIG. 1.

The transmitter 10 employed by the pipeline inspection system 1 of the preferred embodiment has a multi-turn inductor coil. A primary field is produced in the transmitter 10 by the signal generator 20 providing an on-off transmitting current based on a square wave pulse with off-time equal to on-time, as seen in FIG. 3. The off-time is a multiple of 10 ms to provide rejection of 50 Hz mains supply interference that could be induced by underground electrical conductors. The off-time may be varied for areas where 60 Hz supply is used. Measurements of the secondary field are taken when the primary field is inactive. In the preferred embodiment, an off-time of 10 or 20 ms is used for recording a target response but additional multiples of 10 ms are used for highly conductive materials. The power supplied to the signal generator 20 by the two 12 volt batteries contained in the housing 100 gives currents within the transmitter 10 ranging up to 10 amps. This value of transmitter current has been found to provide adequate transmission signal levels. There is no upper limit on transmitter current. However, transmitter current should be kept to a minimum in order to conserve power and therefore to maximize battery life. Actual transmitter currents are measured in each run via the first stage of the receiver/filter 30 so the apparent response can be normalized giving output as microvolts/amp. Flyback voltages generated at switch-off are clamped via a zener diode (not illustrated) or equivalent on each polarity resulting in a controlled ramp to zero. Typical ramp times are 50–100 psec. Off-signal times are recorded from the start of the off-ramp.

The eddy currents are induced in target subsurface conductors (e.g. soils, etc) by the rapidly changing magnetic field produced by terminating the current in the transmitter 10 winding loop. These currents will initially be concentrated at the surface of the target conductor, such that their direction and magnitude preserves the normal component of the magnetic field at the instant the primary current in the transmitting loop is removed.

Eddy currents induced by the primary field at the surface of the target conductor will begin to gradually dissipate by resistive heat loss resulting in a progressive decrease in the magnitude of the secondary magnetic field. The decreasing magnetic field allows the eddy currents concentrated at the surface to begin to flow in towards the center of the conductor. The overall result is a decrease or exponential decay in the amplitude of the magnetic field with time. It is this exponential decay in amplitude of the magnetic component of the secondary field that is measured in the pipeline inspection system 1 of the preferred embodiment.

The receiver elements 2,4,6 measure the target response. The receiver elements 2,4,6 respond to variations in the collapsing magnetic field associated with the current induced in the target conductor at the time of the transmitter switch-off. Consequently output is normally obtained as a voltage induced in the receiver as a time-derivative of the magnetic field.

Figure 4:
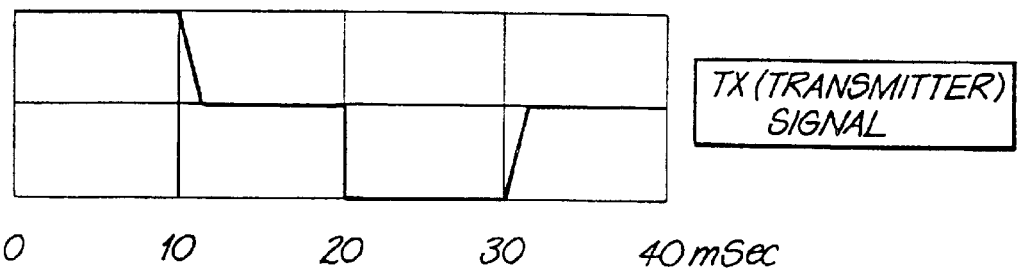
FIG. 4 shows the transmitter and receiver signal waveforms according to the system of FIG. 1.
Figure 4:
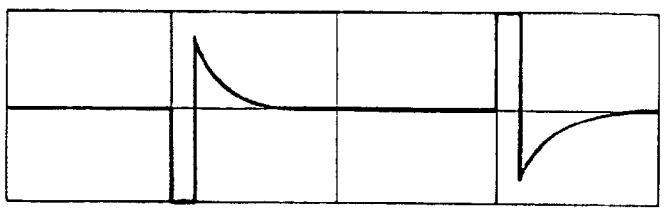

Large spikes are generated in the elements 2,4,6 of the receiver 40 at switch-off, as seen in FIG. 4. The amplitude and duration of the spikes depend on the damping characteristics of the transmitter 10 to provide a controlled ramp to zero. Normally these spikes are sufficient to saturate the variable gain amplifier/filter 30 and mask the true target response until recovery is obtained shortly after the ramp-time is completed (50–104 p.sec).

The eddy currents induced in the target conductor normally decay monotonically to zero after completion of the ramp time of the transmitter 10. The time derivative of the associated magnetic fields are recorded by the receiver 40 during the off-time of the transmitter 10. The polarity depends on the relative orientation of the transmitter 10, the target conductor and the receiver 40 as well as any overprinting of multiple targets. Sign reversals observed during a single delay of an eddy current system are one particular feature of subsurface instability integral to the pipeline survey system.

Figure 5:
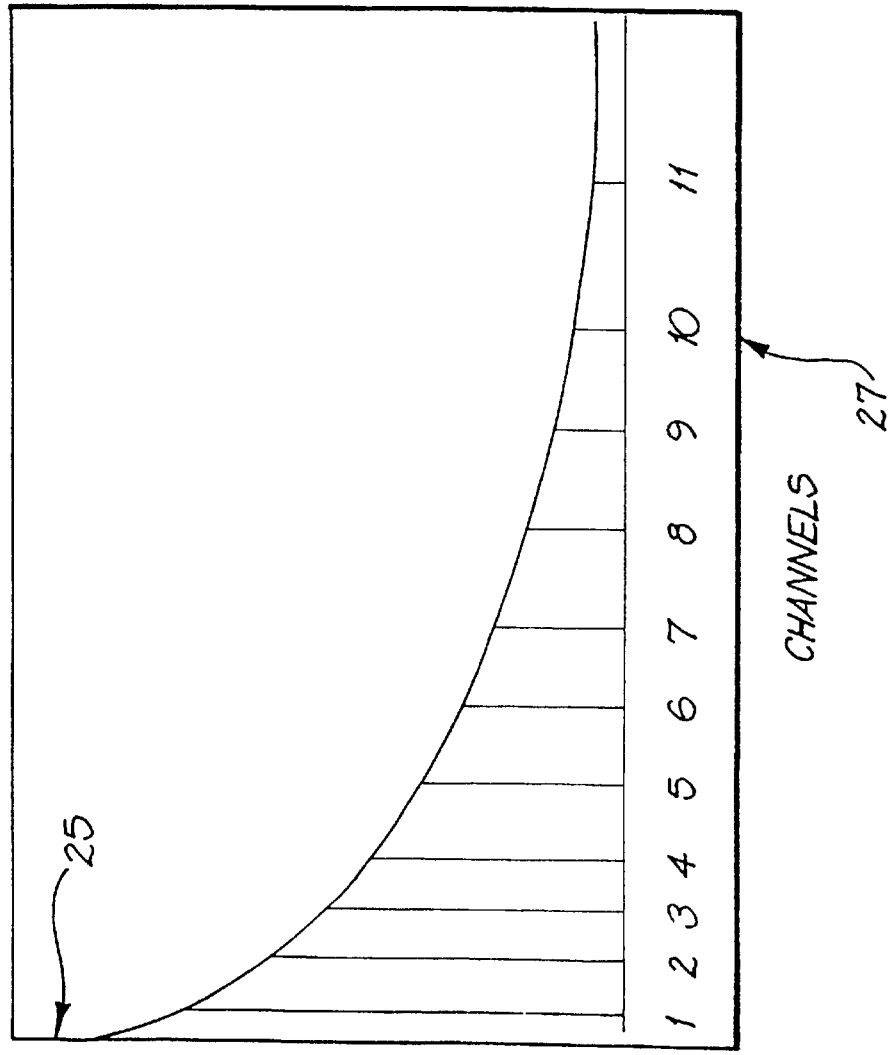
FIG. 5 shows the decay of eddy currents in a target conductor according to the system of FIG. 1.

FIG. 5 shows a graph of the eddy currents induced in the target conductor. The graph has a vertical axis 25 in units of nano-Volts per Ampere and a horizontal axis 27 in units of milliseconds.

As seen in FIG. 5, the eddy currents decay towards zero in a semi-exponential fashion. The rate of decay depends upon the resistivity of the target conductor and consequently the signal is sampled as a function of time. The samples are taken in several discrete intervals described as channels (windows). The number of samples in each channel can be increased progressively, as seen in the table of FIG. 5, to accommodate the exponential decay and ensure sound statistics for averaging at low signal levels late in the decay. This is achieved by progressively increasing the sampling period at each sample with every channel. The instantaneous analogue signal seen by the receiver elements 2,4,6 are amplified and filtered by the variable gain amplifier 30. The signal is then passed to the multiplexer 50 which is controlled by the microprocessor 70 and selects alternative outputs of the amplifier 30 to enable sampling. The individual analogue samples are then converted to an equivalent digital signal by the A/D converter 60 and processed by the microprocessor 70 before being sent serially via the communications cable 65 to the stationary computer 80 using frequency modulation or digital coding. Alternatively, the individual analogue signals may be communicated directly to the stationary computer 80 with the A/D converter 60 attached at the surface.

The individual samples are stored in groups in the memory of the stationary computer 80 and also displayed. At the completion of the sampling process a single average value is calculated for all samples in each channel and a new cycle is initiated. Final estimates for each window are based on linear stacking (or averaging) over numerous cycles (typically 256 repeat cycles) to ensure robust statistics and low noise levels. Samples must be obtained at rates close to 100 kHz to provide satisfactory statistics and noise reduction in each part of the decay.

Figure 7:
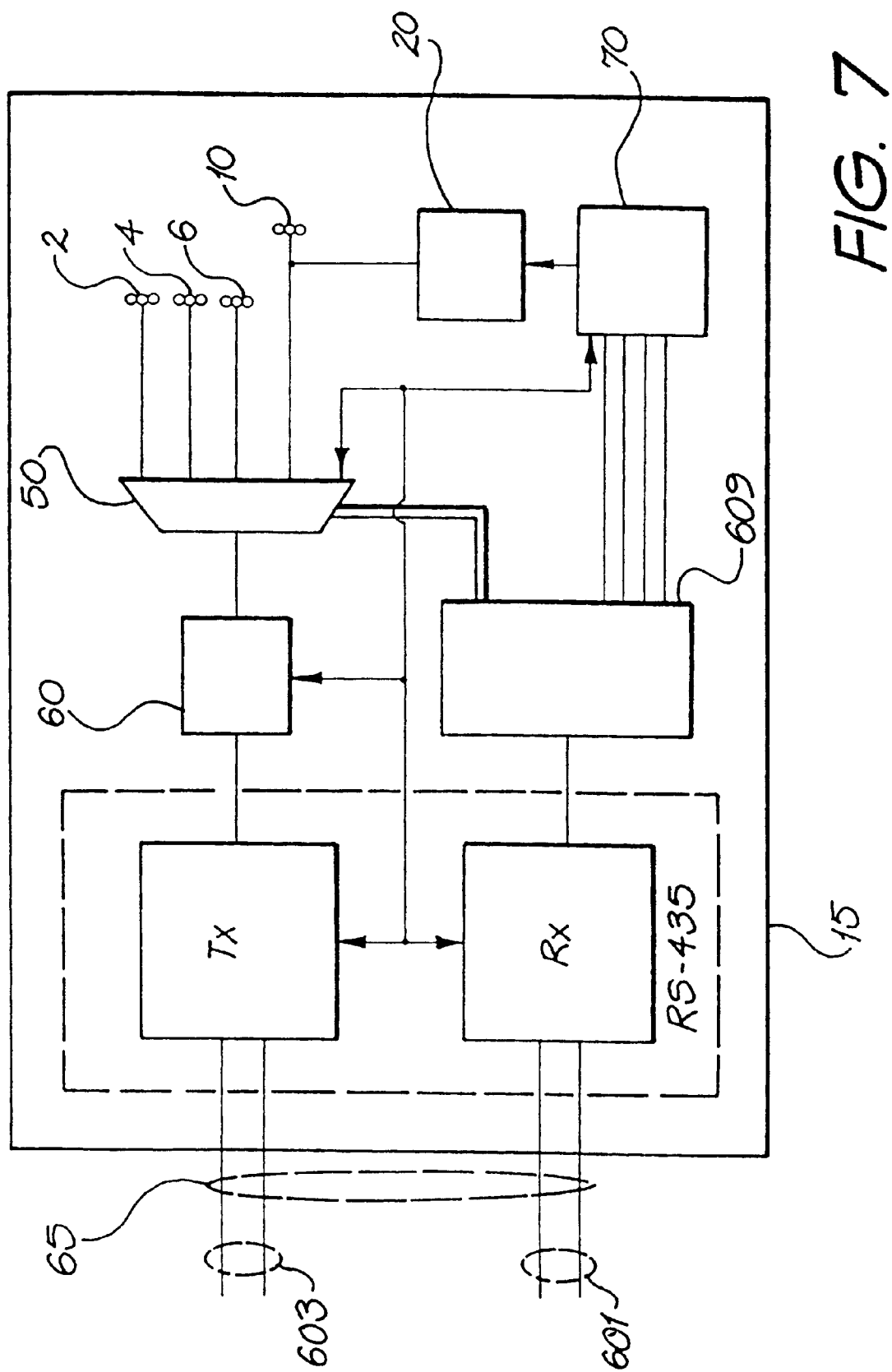
FIG. 7 is a schematic diagram that shows the functionality of the mobile unit inspection system of FIG. 1.

FIG. 7 is a schematic diagram that illustrates the functionality of the mobile unit 1–5. As seen in FIG. 7, the communications cable 65 of the preferred embodiment is a 4core logging cable with RS485 connectors at each end. Two wires 601 of the four wires 65 are used for control signals which are transmitted from the stationary unit 85.

The control signals are read by a decoder 609 which decodes the received signals and communicates the decoded signals to the microprocessor 70 and multiplexer 50. The remaining two wires 603 are for transmission of the target response signal which is measured by the receiver elements 2, 4, 6, and converted to an equivalent digital signal by the A/D converter 60. During transmission, the multiplexer 50, which is controlled by the microprocessor 70 via line 607, is dedicated to the receiver elements 2, 4, 6. When not transmitting, the multiplexer 50 allows for communication of control signals, such as battery power and mobile unit 15 status, from the microprocessor 70 to the stationary unit 85.

Signal levels detected at the receiver 40 range from several mV reducing to several nV within 10 msec. Consequently a 21 bit capacity is required from the A/D converter 60 to ensure adequate resolution. However, at such levels, sample speed can then be seriously degraded. The preferred embodiment uses a strategy based on 12 bit sampling combined with gain ranging. The microprocessor 70 provides appropriate gain settings to the receiver/filters 30 to ensure that the major portion of each decay remains within the 12 bit range of common A/D chips. A full 21 bit equivalent can be provided using gains of $1/1000$, $1/100$, $1/10$, and 1 to scale large amplitudes at early times in the decay, as seen in Table 1 below. Table 1 shows individual receiver values according to one embodiment of the present invention. A single gain step from $1/10$ to 1 can be used if the late sections of the decay are considered to be too noisy. Settling times can cause serious difficulties if the gains are dynamically adjusted during any single decay. Consequently, pre-set gains may be required with suitable selections for each portion of the decay provided via highspeed multiplexing.

TABLE 1

| bits | range | Mult | gain | equiv | pre-amp | gain | equiv |
|---|---|---|---|---|---|---|---|
| 1 | 2 | 1 | 1 | 2 | | | |
| 2 | 4 | 1 | 1 | 4 | | | |
| 3 | 8 | 1 | 1 | 8 | | | |
| 4 | 16 | 1 | 1 | 16 | | | |
| 5 | 32 | 1 | 1 | 32 | | | |
| 6 | 64 | 1 | 1 | 64 | | | |
| 7 | 128 | 1 | 1 | 128 | 0.01 | 1 | 1.28 |
| 8 | 256 | 1 | 1 | 256 | 0.01 | 1 | 2.56 |
| 9 | 512 | 1 | 1 | 512 | 0.01 | 1 | 5.12 |
| 10 | 1024 | 1 | 1 | 1024 | 0.01 | 1 | 10.24 |
| 11 | 2048 | 1 | 1 | 2048 | 0.01 | 1 | 20.48 |
| 12 | 4096 | 1 | 1 | 4096 | 0.01 | 1 | 40.96 |
| 13 | 8192 | 2 | 0.1 | 819.2 | 0.01 | 1 | 81.92 |
| 14 | 16384 | 4 | 0.1 | 1638.4 | 0.01 | 1 | 163.84 |
| 15 | 32768 | 8 | 0.1 | 3276.8 | 0.01 | 1 | 327.68 |
| 16 | 65536 | 16 | 0.01 | 655.36 | 0.01 | 1 | 655.36 |
| 17 | 131072 | 32 | 0.01 | 1310.72 | 0.01 | 1 | 1310.72 |
| 18 | 262144 | 64 | 0.01 | 2621.44 | 0.01 | 1 | 2621.44 |
| 19 | 524288 | 128 | 0.001 | 524.288 | 0.01 | 0.1 | 524.288 |
| 20 | 1048576 | 256 | 0.001 | 1048.576 | 0.01 | 0.1 | 1048.576 |
| 21 | 2097152 | 512 | 0.0001 | 2097.152 | 0.01 | 0.1 | 2097.152 |

Appendix 1 shows a pseudo-code listing of A/D control according to the preferred embodiment.

The above-described embodiment has several advantages over prior art subsurface pipeline inspection methods and over existing commercial TEM systems which are outlined below.

Existing TEM systems used for mineral exploration generally require direct access between a transmitter and a recorder having both positioned in close proximity to an electronic control center. The normal mineral exploration survey systems usually involve a single horizontal transmitter loop with manual advance. Various receiver units are employed but all require fixed cables leading to a central control. Further, some existing TEM systems require transducers to make contact with a sewer wall in order to detect defects in the vicinity of the sewer pipe. However, these arrangements are unsuitable for use in adverse environmental conditions such as an uneven sewer wall or a mine shaft, since these arrangements need a relatively smooth surface to operate efficiently.

The sewerline inspection system 1 of the preferred embodiment enables subsurface resistivity data to be obtained at remote locations under adverse environmental conditions, since the transmitter 10 and receiver coils 2,4,6 are physically isolated from the pipeline wall. The system responds to both pipeline wall defects as well as soil and bedding conditions external to the pipeline which are invisible to normal CCTV inspection systems. Further, the mobile unit 15 of the preferred embodiment is self-powered and processes the electromagnetic response prior to communicating the processed response to the remote stationary unit 85. This aspect of the preferred embodiment further enables the preferred mobile unit 15 access to more remote locations under more adverse environmental conditions, than for existing arrangements.

The preferred embodiment provides a safer method of pipeline inspection with no manual inspections required. Further, all sensitive recording equipment can remain at a fixed surface location. Logistics are simple and high productivity rates can be obtained giving economic advantages over alternative radar and seismic methods.

The foregoing describes only one embodiment of the present invention and modifications can be made thereto without departing from the scope of the present invention. For example, continuous recording based on higher transmit currents combined with an auto-trigger device could be employed in the sewerline inspection system 1 of the preferred embodiment.

Further, a radial transmitter configuration is preferred for pipeline and sewer applications but can include transmitter loops of other geometries. For example, the conduit in which the mobile unit 15 is used does not have to be a sewer pipe and a flat transmitter could be employed for narrow shafts such as in mining operations. A person skilled in the art would appreciate that the mobile unit 15 could be configured to operate in any duct, conduit, pipeline, mining shaft, or the like, of any diameter or cross section.

Still further, a radio transmitter could be employed by the preferred embodiment such that the data samples could be communicated from the housing 100 to the stationary computer 80 via radio waves or optical cable.

Still further, the housing 100 of the preferred embodiment is cylindrical in nature. A housing of another geometry such as a box configuration could be employed. The housing could also be constructed of an alternative material such as PTFE.

Still further, the communications cable 65 of the preferred embodiment is a 4-wire logging cable with RS485 connectors at each end. Alternatively, a 2-wire communication cable with any suitable communications protocol can be utilized including RS232.

APPENDIX 1

```
A/D Control
Open CPU Menu

Set survey parameters
    Set save-five name:
        Set co-ordinates X: (1–10000)
        Set co-ordinates Y: (1–10000)
    Set A/D parameters
        Set number of Windows required (1–26)
        Set number of stacks (1–1024)
        Set number of components (1–3)
Write to local comms RS485
Start µP Control Read remote comms 485
    Get A/D parameters
For component i=1–3
For stack number = count
    Start +ve transmitter signal if on-time >10 msec
        Get transmitter current
        Commence transmitter ramp to zero
    for n=1 to 1000 (=10 msec)
        Get psample(i,n) for lo-gain channel
        if abs sample (n) <500 else repeat
            Get psample(i,n) for hi-gain channel
    Normalise for transmitter current
    Start –ve transmitter signal if on-time >10 msec
        Get transmitter current
        Commence transmitter ramp to zero
    for n=1 to 1000 (=10 msec)
        Get nsample(i,n) for lo-gain channel
        if abs sample (n) < 500 else repeat
            Get nsample(i,n) for hi-gain channel
    Normalise for transmitter current
    Add psample and nsample to tsample
If count < stacks repeat
Write tsamples to RS485 and store on CPU
If all components finished Exit to CPU
Return to CPU Calculate window averages
Display decay curves
Toggle to view numerical data
Toggle to display profile
Toggle to view different component
ESC to CPU menu
```

What is claimed is:

1. A time domain electromagnetic (TEM) subsurface analysis system for the analysis of a conduit and the geological surrounding of said conduit wherein at least part of said system is configured for insertion along said conduit and for the emission of a varying primary magnetic field and the reception and measurement of an electromagnetic response thereto in the form of a decaying secondary magnetic field influenced by said geological surrounding.

2. The time domain electromagnetic (TEM) subsurface analysis system according to claim 1, wherein said conduit is substantially non-ferrous.

3. The time domain electromagnetic (TEM) subsurface analysis system according to claim 1, said system comprising a waveform generator configured to produce said TEM signals.

4. The time domain electromagnetic (TEM) subsurface analysis system according to claim 1, wherein said part of said system is operatively coupled to a stationary controller and TEM recorder module.

5. The time domain electromagnetic (TEM) subsurface analysis system according to claim 4, wherein said system is configured to utilise at least one of frequency modulation, amplitude modulation and digital coding for communication between said part of said system and said stationary controller.

6. The time domain electromagnetic (TEM) subsurface analysis system according to claim 4, wherein said part of said system is coupled to said stationary controller via a physical communication channel.

7. The time domain electromagnetic (TEM) subsurface analysis system according to claim 6, wherein said part comprises an integral power source and said communications channel comprises one of a two-wire cable, a four-wire cable and an optical fibre cable.

8. The time domain electromagnetic (TEM) subsurface analysis system according to claim 1, wherein said part of said system comprises at least one transmitter coil and a plurality of receiver coils that are configured as part of a mobile module.

9. The time domain electromagnetic (TEM) subsurface analysis system according to claim 8, wherein said transmitter coil is formed as a radial winding around one end of said mobile module.

10. The time domain electromagnetic (TEM) subsurface analysis system according to claim 8, wherein said receiver coils are mutually perpendicular to each other.

11. The time domain electromagnetic (TEM) subsurface analysis system according to claim 1, wherein said electromagnetic response is processed prior to communicating the processed response to said stationary controller.

12. The time domain electromagnetic (TEM) subsurface analysis system according to claim 8, further comprising a multiplexer arrangement for coupling at least said receiver coils in a predetermined manner to said stationary controller.

13. The time domain electromagnetic (TEM) subsurface analysis system according to claim 1, wherein said conduit is a sewer pipe.

14. An inspection system for the analysis of a duct and the geological surrounding of said duct, said system comprising:
    a first apparatus configured for insertion into said duct and comprising:
        (i) transmission means for transmitting a varying primary magnetic field inducing an electromagnetic response thereto in the form of a decaying secondary magnetic field influenced by said duct and material surrounding said duct,
        (ii) detection means for detecting and measuring said electromagnetic response;
        (iii) conversion means for converting said electromagnetic response to a discrete signal; and
        (iv) conmmunication means for reading and communicating said discrete signal to a second apparatus positioned remotely to said first apparatus;
    said second apparatus comprising:
        (i) storage means for storing said discrete signal;
        (ii) processor for processing said discrete signal; and
        (iii) display for displaying said processed discrete signal.

15. The inspection system according to claim 14, wherein said electromagnetic response is processed prior to communicating the processed response to said stationary controller.

16. The inspection system according to claim 14, wherein said first apparatus comprises at least one transmitter coil and a plurality of receiver coils.

17. The inspection system according to claim 16, said first apparatus further comprising a multiplexer arrangement for coupling at last said receiver coils in a predetermined manner to said second apparatus.

* * * * *